(12) United States Patent
Crockatt et al.

(10) Patent No.: US 10,562,837 B2
(45) Date of Patent: Feb. 18, 2020

(54) PREPARATION OF PHENYL COMPOUNDS

(71) Applicant: Nederlandse Organisatie voor toegepast-natuurwetenschappelijk onderzoek TNO, The Hague (NL)

(72) Inventors: Marc Crockatt, The Hague (NL); Jan Harm Urbanus, The Hague (NL); Paul Mathijs Könst, The Hague (NL)

(73) Assignee: Nederlandse Organisatie voor toegepast-natuurwetenschappelijk onderzoek TNO, The Hague (NL)

( * ) Notice: Subject to any disclaimer, the term of this patent is extended or adjusted under 35 U.S.C. 154(b) by 0 days.

(21) Appl. No.: 16/064,287

(22) PCT Filed: Dec. 22, 2016

(86) PCT No.: PCT/NL2016/050915
§ 371 (c)(1),
(2) Date: Jun. 20, 2018

(87) PCT Pub. No.: WO2017/111598
PCT Pub. Date: Jun. 29, 2017

(65) Prior Publication Data
US 2019/0010111 A1 Jan. 10, 2019

(30) Foreign Application Priority Data
Dec. 22, 2015 (EP) ..................... 15202135

(51) Int. Cl.
| | | |
|---|---|---|
| *C07D 307/00* | (2006.01) | |
| *C07C 67/31* | (2006.01) | |
| *C07C 37/50* | (2006.01) | |
| *C07C 309/42* | (2006.01) | |
| *C07C 309/58* | (2006.01) | |
| *C07C 51/09* | (2006.01) | |
| *C07C 309/32* | (2006.01) | |
| *C07C 303/22* | (2006.01) | |
| *C07C 309/44* | (2006.01) | |
| *C07C 309/75* | (2006.01) | |
| *C07C 309/77* | (2006.01) | |

(52) U.S. Cl.
CPC ............. *C07C 67/31* (2013.01); *C07C 37/50* (2013.01); *C07C 51/09* (2013.01); *C07C 303/22* (2013.01); *C07C 309/32* (2013.01); *C07C 309/42* (2013.01); *C07C 309/44* (2013.01); *C07C 309/58* (2013.01); *C07C 309/75* (2013.01); *C07C 309/77* (2013.01); *C07D 307/00* (2013.01)

(58) Field of Classification Search
CPC ....... C07C 67/31; C07C 37/50; C07C 309/42; C07C 309/58; C07C 309/75; C07C 51/09; C07C 309/77; C07D 307/00
USPC ...................................................... 549/463
See application file for complete search history.

(56) References Cited

U.S. PATENT DOCUMENTS

| | | | | |
|---|---|---|---|---|
| 3,335,176 | A * | 8/1967 | Pietrusza ............... | C07C 229/38 |
| | | | | 528/325 |
| 3,891,633 | A | 6/1975 | Berlin et al. | |
| 5,773,439 | A | 6/1998 | Lubisch et al. | |
| 7,235,559 | B1 * | 6/2007 | Mortlock ............... | C07D 239/94 |
| | | | | 514/266.2 |
| 2013/0336920 | A1 * | 12/2013 | Lewis ................... | C07D 213/81 |
| | | | | 424/78.38 |

FOREIGN PATENT DOCUMENTS

| | | | | |
|---|---|---|---|---|
| JP | 06128812 | A | * | 5/1994 |
| RU | 2135464 | | * | 8/1999 |

OTHER PUBLICATIONS

Lee et al, Molar-Ratio-Dependent Supramolecular Isomerism: AgI Coordination Polymers with Bis(cyanobenzyl)sulfides, Chemistry—a European Journal, 2013, 19(41), p. 13638-13645. (Year: 2013).*
Reed et al, Nucleophilicities of Selected Ions in Water at 195° C., J. Org. Chem. 1993, 58, p. 6372-6376. (Year: 1993).*
Ono et al, Preparation of Stable 5,15-Dihydroporphyrin, Bull. Chem. Soc. Jpn., 1991, 64, p. 3471-3472 (a cpoy of 2 pages). (Year: 1991).*
Bregman et al, Aromatic Sulphonation. Part 76.1 Sulphonation in Sulphuric Acid of w-Phenylalkanes containing the NH3+, NMe3+, or NO2 Substituent at Position 1. Comparison of the Side-chain NH3+,Journal of the Chemical Society , Perkin Transactions 2: Physical Organic Chemistry (1972-1999), 1980, (1), p. 33-38.*
Steinkof et al , Journal fuer Praktische Chemie (Leipzig), 1927, 117, 1-82, (abstract page ). (Year: 1927).*
Hujun et al., Synthesis and Properties of a Novel Linear Alkylated Diphenylmethane Sulfonate Gemini Surfactant, J. Surfact. Deterg., 16:57-61, 2013.
Moreno et al., An Efficient One-Pot Synthesis of Phenol Derivaties of Ring Opening and Rearrangement of Diels-Alder Cycloadducts and Substituted Furans Using Heterogeneous Catalysis and Microwave Irradiation, Synlett, No. 7, pp. 1259-1263, 2004.
Holmes et al., CCXL—The Nature of the Alternating Effect in Carbon Chains. Part III. A Comparative Study of the Directive Efficiencies of Oxygen and Nitrogen Atoms in Aromatic Substitution, J. Chem. Soc., Trans., 1800-1821, 1925.
Grützmacher et al., [3.2] Paracyclophane-10-enes and [3.2.3.2] Paracyclophane-10,27-dienes: A Convenient Synthesis by the McMurry Reaction and dynamic Sterochemistry, Chem. Ber. 122, pp. 2291-2297, 1989.
Zolfigol, Mohammad Ali et al., "The use of Nafion-H as an efficient catalyst for the direct conversion of primary and secondary trimethylsilyl ethers to their corresponding ethers under mild and heterogeneous conditions", Tetrahedron Letters, vol. 44, No. 44 (Oct. 27, 2003), pp. 8165-8167, DOI: 10.1016/j.tetlet.2003.09.036.
Simonis, H., "Berichte der deutschen chemischen Gesellschaft", vol. 45, No. 2 (May 1, 1912), pp. 1584-1592.

* cited by examiner

*Primary Examiner* — Taylor V Oh
(74) *Attorney, Agent, or Firm* — Verrill Dana, LLP

(57) ABSTRACT

The invention relates to a method for preparing a compound comprising two phenyl groups by reacting a bisfuranic compound with a dienophile; and to such compounds.

14 Claims, No Drawings

PREPARATION OF PHENYL COMPOUNDS

The present invention relates to the preparation of compounds comprising two phenyl groups, such as bisphenol compounds.

Bisphenol compounds comprise two hydroxyphenyl groups linked by a linking moiety. They are generally prepared by the condensation of an aldehyde or a ketone with two equivalents of phenol or cresol. More generally, bisphenyl compounds, comprising two optionally substituted phenyl groups linked by a linking moiety or a covalent bond, can be prepared in a similar way. Current commercial processes for the production of phenol for this process are typically based on the oxidation of petrochemical cumene derivatives, to yield the desired phenol and acetone (a waste product in the process). Cresols are most commonly isolated from coal tar.

Incidentally, European Journal of Organic Chemistry, 2015(28), 6146-6151; 2015 describes the reaction of bis-(furan-2-yl)methanes to conjugated nitroso and azoalkenes giving hetero Diels-Alder adducts. This method does not provide compounds comprising two phenyl groups.

In view of the various limitations and disadvantages of current preparation methods of bisphenol compounds, it would be advantageous to provide methods for the preparation of bisphenol compounds that use compounds obtainable from bio-renewable sources. Such compounds do not have a petrochemical origin. The same applies for other bisphenyl compounds comprising two phenyl groups linked by a linking moiety or a covalent bond.

In order to address one or more of the above mentioned desires at least in part, the present invention provides a method for preparing such bisphenyl compounds. Accordingly, the present invention relates to a method for preparing a compound comprising two phenyl groups by reacting a bisfuranic compound with a dienophile. The prepared compound comprising two phenyl groups is for example a bisphenol. As used herein, the term "bisfuranic compound" refers to a compound comprising two furanic moieties.

Compared to a possible alternative method of reacting a furanic compound into an aromatic compound and reacting two aromatic compounds to give a bisphenyl, the method of the invention allows for more efficient use of the expensive dienophile. In addition, the method of the invention makes efficient use of the catalyst.

Without wishing to be bound by way of theory, the reaction is believed to involve a cycloaddition wherein an intermediate adduct is formed with a bicyclic adduct for each furanic moiety, and in situ ring opening to provide phenyl groups. For instance, the reaction may involve Diels-Alder cycloaddition. However, some embodiments involve obtaining a bicyclic product and ex situ ring opening thereof. It will be appreciated that the present invention is directed to any reaction of the bisfuranic compound with a dienophile, independently of the specific reaction pathway or mechanism involved. For instance, although the Diels-Alder reaction is a concerted reaction, viz. a single-step reaction without any intermediate, a non-concerted reaction such as e.g. a Friedel-Craft-type pathway is also within the scope of the present invention.

The bisfuranic compound is for example prepared from a furanic compound. A furanic compound comprises as backbone structure:

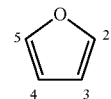

for example substituted on the 2, 3, 4 and/or 5 position by one or more groups such as alkyl chains, heteroatoms and/or halogens. Said alkyl chains are typically $C_1$-$C_8$-alkyls and can be linear or branched and can be optionally substituted by halogens and/or heteroatoms. The furanic compound may be bound to a solid support so that purification after a reaction may be facilitated.

Furanic compounds can be obtained for instance from biomass according to known methods. Furanic compounds can be converted into a bisfuranic compound for instance by the acidic condensation of furanic compounds with an aldehyde or ketone, according to known methods, for instance as described in European Journal of Organic Chemistry, 2015(28), 6146-6151; 2015.

Further methods for the preparation of bisfuranic compounds from furanic compounds are for instance described in Journal of Applied Polymer Science, 131(24), 40179/1-40179/5; 2014; Chemistry—A European Journal, 6(22), 4091-4103; 2000; Journal of Molecular Catalysis, 57(1), 91-103; 1989; Journal of the Chemical Society, Perkin Transactions 1, (14), 1631-1643; 2002; Journal of Organic Chemistry, 68(7), 2964-2967; 2003; and Synthesis, (9), 1253-1258; 2000; Synthetic Communications, 34(23), 4249-4256; 2004; Heteroatom Chemistry, 25(6), 548-555; 2014; and Journal of Organic Chemistry, 68(7), 2964-2967; 2003.

The bisfuranic compound generally comprises a backbone structure according to formula (I), preferably according to formula (I).

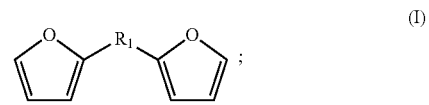

wherein $R_1$ can be any suitable linking group or can be a covalent bond, and wherein the furanic moieties are optionally substituted. Such compounds can also be referred to as bisfuranic compounds. Herein, the term "backbone structure" means that the formula schematically represents a core structure of a group of compounds, which can additionally be substituted with any group or atom at any position.

$R_1$ is for example such that the furanic moieties are spaced by a covalent bond, or 1, 2, 3, 4, 5 or 6, or more atoms, wherein accordingly the shortest connection between the furanic moieties has such number of atoms. $R_1$ is preferably a divalent moiety. If $R_1$ is a covalent bond, the furanic moieties are joined by a covalent bond and are not spaced by an atom. An example of a preparation method for a bisfuranic compound wherein $R_1$ is a covalent bond is given in Organic Letters, 16(10), 2732-2735; 2014.

$R_1$ can for instance be a linking group having 1, 2, 3, 4, 5 or 6 atoms linking atoms defining the shortest connection between the furanic moieties, or 7 to 20 linking atoms, or more linking atoms, wherein the linking atoms are preferably selected from the group consisting of C, N, O, and S.

R₁ can for example comprise —C—, —O—, —N— or —S—; —C—C—, —C—O—, —C—N—, or —C—S—, or —C—C—C—, —C—O—C—, —C—N—C—, or —C—S—C— as linking unit between the furanic moieties, the linking atoms optionally having substituents, such as R₃ as defined hereinafter, as appropriate, wherein the indicated bonds are preferably single bonds.

R₁ preferably comprises —C—, —C—C—, or —C—O—C— as linking atoms, wherein R₁ optionally consists of hydrogen and 1 to 20, 1 to 12 or 1 to 6 atoms selected from C, N, O and S, more preferably selected from C and O.

The furanic moieties are optionally, independently, substituted or unsubstituted and can be the same or different. Substitution is preferably at the 3, 4 and/or 5 position (if the 2 position is substituted with R₁), for example at least at the 5 position. Such substitution is preferably with one or more alkyl groups, heteroatoms and/or halogens, more preferably with alkyl groups, typically with linear or branched $C_1$-$C_8$ alkyls. Any such alkyl substituents can be further substituted by halogens and/or heteroatoms, such as O, N, S and P.

R₁ can comprise one or more additional furanic groups, such that the bisfuranic compound has three or more furanic groups. The reaction can also comprise conversion of these groups into phenyl groups. This gives a compound comprising three or more phenyl groups.

The linking group R₁ can for example be such that the furanic groups are at least formally substituted onto for example a sulfone, alkyl, aromatic or cyclic aliphatic compound. The linking group can for example correspond to the linking groups of commercially available bisphenols such as bisphenol M (1,3-bis(2-(4-hydroxyphenyl)-2-propyl)benzene), bisphenol S (bis(4-hydroxyphenyl)sulfone), bisphenol P (1,4-bis(2-(4-hydroxyphenyl)-2-propyl)benzene), bisphenol PH (5,5'-(1-methylethyliden)-bis[1,1'-(bisphenyl)-2-ol]propane). The method can for instance result in such bisphenol compounds as product.

Preferably, the bisfuranic compound is formally a diphenylmethane derivative. Accordingly, R₁ is preferably an optionally substituted methyl group.

Accordingly, the bisfuranic compound preferably has formula (IIa)

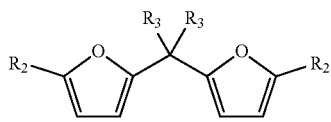

(IIa)

wherein each R₂ is independently H, a heteroatom, a halogen, or linear or branched $C_1$-$C_8$ alkyl, wherein said alkyl is optionally further substituted by halogens and/or heteroatoms. In some embodiments, at least one of said R₂ is not hydrogen. More preferably, each R₂ is independently selected from the group consisting of H, Me, F, Cl, Br, I, —CH₂F, —CH₂Cl, —CH₂Br, —CH₂I, —CN, —NO₂, —CH₂NH₂ and amides thereof, —CH₂OH and esters or ethers thereof and —CO₂H and esters thereof. R₂ can for example comprise one or more additional furanic groups which may also be converted into phenyl group.

Each R₃ is preferably independently selected from the group consisting of H, a halogen, a heteroatom functional group and an optionally substituted and/or optionally heteroatom containing $C_1$-$C_{40}$ hydrocarbyl group, which can be for instance cyclic, linear or branched, such as alkyl, alkenyl, alkaryl, aryl, or cycloalkyl, in particular $C_1$-$C_{12}$ alkyl, $C_2$-$C_{12}$ alkenyl, $C_3$-$C_{12}$ cycloalkyl, or $C_6$-$C_{10}$ monocyclic or bicyclic aryl. Said $C_1$-$C_{40}$ hydrocarbyl is hence for instance selected from the group consisting of alkyl, alkenyl, alkaryl, aryl, and cycloalkyl; and is for example $C_1$-$C_{12}$ alkyl, $C_2$-$C_{12}$ alkenyl, $C_3$-$C_{12}$ cycloalkyl, or $C_6$-$C_{10}$ monocyclic or bicyclic aryl, wherein each of said groups is optionally substituted. The hydrocarbyl group is optionally substituted by for example a halogen, a heteroatom functional group a $C_1$-$C_{12}$ alkyl, or a $C_2$-$C_{12}$ alkenyl. The R₃ groups can be the same or different. Optionally, at least two of said R₃ can also be joined to form a ring, for example to form an aryl or cycloalkane group, such as cyclohexane. The R₃ groups on the same carbon atom can also form one double bounded substituent, such as an alkene, imine, or carbonyl group. In a heteroatom containing hydrocarbyl group, one or more carbon atoms are replaced by a heteroatom such as O, N, S and P. Suitable heteroatom functional groups for example comprise O, N, S and/or P, and are for example selected from the group consisting of hydroxyl, carbonyl (═O), aldehyde, esters, carboxyl, alkoxy, ethers, acetal, ketal, amine, imine, cyanate, thiol, sulphide, sulfino, sulfo, phosphono and phosphate.

The R₃ groups are for example selected such that they correspond to the linking groups of commercially available bisphenol compounds, for example:
Bisphenol A (2,2-bis(4-hydroxyphenyl)propane)
Bisphenol AP (1,1-bis(4-hydroxyphenyl)-1-phenyl-ethane)
Bisphenol AF (2,2-bis(4-hydroxyphenyl)hexafluoropropane)
Bisphenol B (2,2-bis(4-hydroxyphenyl)butane)
Bisphenol BP (bis-(4-hydroxyphenyl)diphenylmethane
Bisphenol C1 (2,2-bis(3-methyl-4-hydroxyphenyl)propane)
Bisphenol C2 bis(4-hydroxyphenyl)-2,2-dichlorethylene)
Bisphenol E (1,1-bis(4-hydroxyphenyl)ethane),
Bisphenol F (bis(4-hydroxyphenyl)methane),
Bisphenol TMC (1,1-bis(4-hydroyphenyl)-3,3,5-trimethyl-cyclohexane) and
Bisphenol Z (1,1-bis(4-hydroxyphenyl)-cyclohexane).

In some embodiments, the method is for preparing such bisphenol compounds.

In a preferred embodiment, the bisfuranic compound has formula IIa and R₃ is selected from the group consisting of hydrogen, hydroxyl, carbonyl (═O) and methyl.

The bisfuranic compound can also for example be a compound according to formula IIb or IIc:

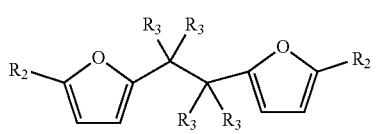

(IIb)

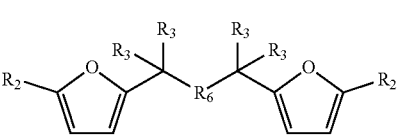

(IIc)

In case of formula IIc, R₆ is selected from the group consisting of a heteroatom functional group and a cyclic, linear or branched $C_1$-$C_{40}$ hydrocarbyl group, optionally containing a heteroatom and/or optionally substituted by halogens and/or heteroatom functional groups, for example as defined for R₃. Preferably R₆ has one linking atom such that the furanic moieties are spaced by three atoms. Preferably, the hydrocarbyl group is an alkyl, alkenyl, alkayrl or aryl group. $R_6$ can for example be selected from the group consisting of heteroatom functional groups, $C_1$-$C_6$ alkyl, $C_2$-$C_6$ alkenyl, and a phenyl group, wherein said alkyl or alkenyl or phenyl is optionally further substituted by halogens and/or heteroatoms. Suitable heteroatom functional groups as $R_6$ are for example —O—, —NR—, —S—, —SO—, —SO$_2$—, —PR—, —BOR— and phosphate, wherein R is for example as defined for $R_3$. Preferably, $R_6$ is —O—, such that the bisfuranic can for example be prepared by standard ether chemistry.

Preferably, $R_6$ has one linking atom, bound to both carbon atoms having $R_3$ substituents, such that the furanic moieties are spaced by three atoms. The linking atom of $R_6$ can for example be O, N, S or C.

In a preferred embodiment, the bisfuranic compound is prepared from by dimerization of furfural, and has formula (IIb), wherein $R_3$ is for example selected such that each of the two carbon atoms of the linking group is provided with a hydroxyl or a carbonyl group, or with no substituent.

The bisfuranic compound is preferably prepared by dimerization of furfuryl alcohol or by reaction of furan with a ketone and/or aldehyde, and/or furfuryl alcohol.

The bisfuranic compound can also have for example a structure according to formula IId:

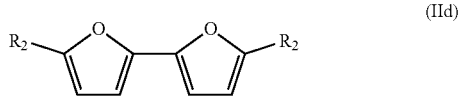

(IId)

Such compounds can for example be prepared by reacting two furanic compounds or dimerization of a furanic compound, for example Chemische Berichte, 114(11), 3667-73; 1981 and Organic Letters, 16(10), 2732-2735; 2014.

The dienophile is generally an alkyne or an alkene, preferably an alkene according to formula IIIa or an alkyne according to formula IIIb:

(IIIa)

or

(IIIb)

wherein $R_5$ preferably is an electron withdrawing group EWG. $R_4$ is preferably H, linear or branched $C_1$-$C_8$-alkyl, or EWG, more preferably H. Preferably each EWG is independently selected from the group consisting of —CN, —NO$_2$, —CO$_2$X, —C(O)NX, —C(=NY)X, CF$_3$, CCl$_3$, CBr$_3$, CI$_3$, —SO$_2$X, —SO$_3$X, —COH, —COX, —COF, —COCl, —COBr, —COI, wherein X and Y are independently selected from the group consisting of H, and linear or branched $C_1$-$C_8$-alkyl, optionally substituted with halogens and optionally supported on a heterogeneous support or polymer-supported. Preferably, $R_4$ is hydrogen, more preferably $R_5$ is —CO$_2$X, wherein more preferably the dienophile is an alkene according to formula IIIa.

In case the dienophile is the alkyne according to formula IIIb, $R_5$ may also be selected from the same group as $R_3$, i.e. the group consisting of H, a halogen, a heteroatom functional group and an optionally substituted and/or optionally heteroatom containing $C_1$-$C_{40}$ hydrocarbyl group.

In a particular embodiment, the alkyne is not activated and $R_4$ and $R_5$ together comprise a total of 0 to 3 carbon atoms and are independently selected from the group consisting of hydrogen, methyl, ethyl, CH$_2$X, OMe, OEt, OiPr and OnPr, wherein X is selected from the group consisting of NH$_2$, NHMe, NMe$_2$, NHEt, NEt$_2$ NHC(O)Me, OH, OMe, OEt, OC(O)Me, SH, SMe, SEt, SOMe, SO$_2$Me and halogen. As used herein, Me stands for methyl, Et for ethyl, iPr for isopropyl and nPr for normal propyl.

The dienophile is for example a propiolate, such as methyl propiolate. The dienophile for example has only one alkene or alkyne group capable of reacting with the bisfuranic compound. Optionally, $R_4$ and $R_5$ are joined to form a ring, although in a preferred embodiment $R_4$ and $R_5$ are not joined to form a ring.

However, other alkynes without an electron withdrawing group (EWG) can also be used. Accordingly, for an alkyne dienophile, $R_5$ can for example also be selected from the same group as $R_3$, and/or the group consisting of hydrogen, methyl, ethyl, CH$_2$X, OMe, OEt, OiPr and OnPr, wherein X is selected from the group consisting of NH$_2$, NHMe, NMe$_2$, NHEt, NEt$_2$ NHC(O)Me, OH, OMe, OEt, OC(O)Me, SH, SMe, SEt, SOMe, SO$_2$Me and halogen. For alkynes with $R_5$ being an alkyl, good results have been obtained with catalysts that are based on gold(I) complexes as described by Echavarren et al., Chem. Eur. J. 19 (2013) 6581-6585 (which is incorporated herein in its entirety), In the dienophile, the double or triple bond of the dienophile is generally between two carbon atoms. This provides for the formation of phenyl groups rather than, for example, pyridines. Hence, in some embodiments, the reaction between the bisfuranic compound and the dienophile does not involve a hetero Diels-Alder reaction.

The prepared compound generally comprises a backbone structure according to formula (IV):

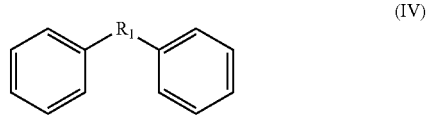

(IV)

wherein each atom of the phenyl groups other than the atom connected with R1 is optionally substituted, for example with $R_2$, $R_4$, $R_5$ and hydroxyl.

More preferably, the product of the reaction of the bisfuranic compound and the dienophile comprises a mixture of various regio-isomers having the general formula:

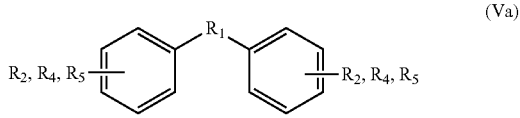

(Va)

if an alkene dienophile is used; and

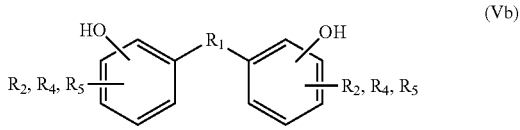

(Vb)

if an alkyne dienophile is used, wherein $R_2$, $R_4$, and $R_5$ are as defined for the bisfuranic compound and the dienophile; wherein $R_4$ is ortho substituted to $R_5$; wherein generally $R_1$, $R_2$, $R_4$ and $R_5$ are substituted to different carbon atoms of the phenyl ring, and wherein —OH is preferably para to $R_1$.

In case an alkyne dienophile is used, the two phenyl moieties can for example independently have as structure any of:

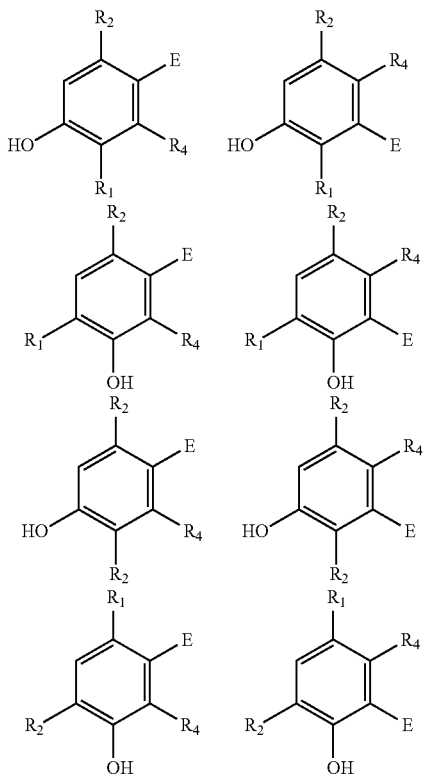

wherein E is EWG or $R_5$, $R_1$ is the linking group, and $R_2$ and $R_4$ are as defined for the bisfuranic compound and the dienophile. Similarly, regio-isomers can be obtained if an alkene dienophile is used.

If an alkyne dienophile is used and $R_2$ and $R_4$ are all hydrogen, the reaction between the dienophile and the bisfuranic compound preferably gives a bisphenol compound, preferably having formula VII,

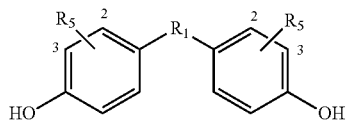

wherein in each phenyl group, $R_5$ is independently at the 2 or 3 position, giving as preferred products:

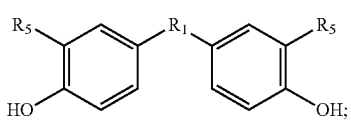

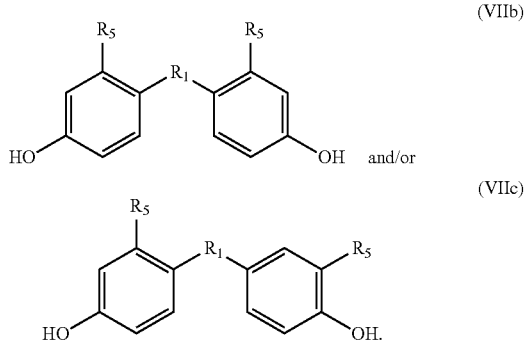

The method optionally comprises modification of the $R_5$ group or removal of the $R_5$ group using known methods. Herein $R_5$ is provided by the alkyne dienophile. In a preferred embodiment, the product of the method of the invention is a bisphenol compound having formula (VII) wherein each $R_5$ is H, for example but not restricted to bisphenol A, B, C, E, F or Z.

Bisphenols A, B, E, F and Z may be obtained by the present invention using the following synthetic pathway:

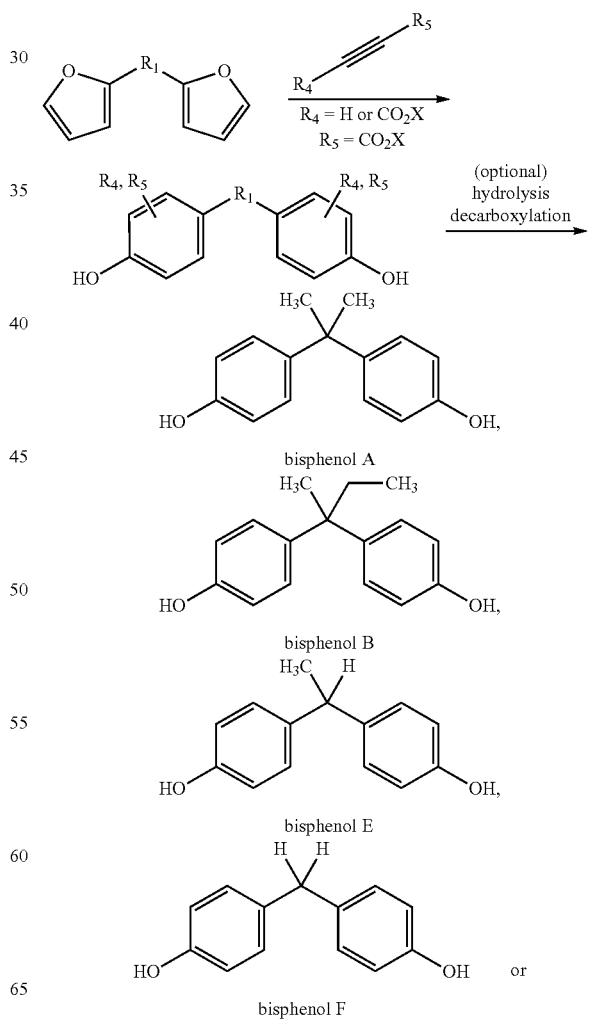

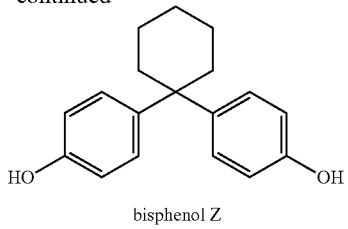

bisphenol Z

By selecting the appropriate $R_1$ group in the starting bisfuranic compound, the same strategy can be used to obtain other bisphenols such as bisphenols AP, AF, BP, C2 and TMC.

Bisphenol C1 may be obtained by the present invention using the following synthetic pathway:

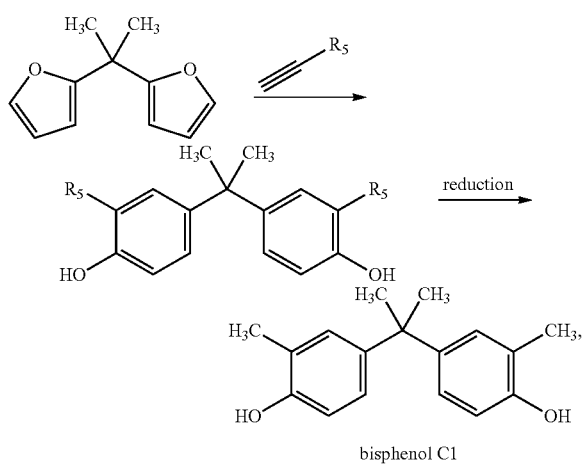

bisphenol C1 wherein $R_5$=an EWG selected from the group consisting of —CN, —CO$_2$X, —C(O)NX, —C(=NY)X, —COH, —COX, —COF, —COCl, —COBr and —COI, preferably wherein $R_5$ is —CO$_2$X. In case $R_5$ is not an EWG but a methyl, bisphenol C1 may directly be obtained without the reduction step.

In the embodiments wherein a product according to formula Vb is obtained and $R_2$, $R_4$ and $R_5$ are not all hydrogens, it may be preferred to remove the substituents $R_2$, $R_4$ and $R_5$, i.e. to replace them by hydrogen. For instance, in case $R_2$ and $R_4$ are hydrogen and $R_5$ is an EWG such as —CO$_2$X, as defined herein above for formula IIIb, the group $R_5$ can be removed by a decarboxylation reaction. In case X is not hydrogen, an intermediate hydrolysis reaction may also be performed.

Decarboxylation may be carried out by catalysis or mediation by metal salts, soda lime, and/or high boiling amines. Metal salt catalysis or mediation is for instance described in Maiti et al., *Org. Biomol. Chem.*, 14, 2016, 21-35, which is incorporated herein by reference. Examples of suitable metal catalysts or mediators for the decarboxylation include Hg, Cu, Pd, Ru, Ag, Au, Fe.

Decarboxylation of a compound according to formula VIIb, wherein $R_5$ is —CO$_2$H may be carried out with for instance Cu$_2$O, see e.g. U.S. Pat. No. 9,517,987, which is incorporated herein by reference.

Decarboxylation condition which may also be suitable for the present invention are reported in Goosen et al., *J. Org. Chem.*, 2009, 74, 2620-2623, which is incorporated herein in its entirety. It was found that Cu$_2$O as the copper source and 1,10-phenanthroline gave particularly good results in the reactions to provide bisphenols according to the present invention.

Enzymatic decarboxylation can also be used. Some benzoic and phenolic acid decarboxylases are mentioned in Org. Lett. 2012, 14 (8), 1974-1977. For instance 4-hydroxybenzoate decarboxylase, salicylic acid decarboxylase and 3,4-dihdyroxy benzoate decarboxylase are known enzymes. Transition metal-catalyzed non-oxidative decarboxylation reactions are described by Liu et al. in Biochemistry, 2006, 45 (35), 10407-10411. The use of an enzyme as catalyst for the selective production of phenol from salicylic acid has been described by Kirimura et al. in Biochem. Biophys. Res. Commun. 2010, 394 (2), 279-284. The enzymatic decarboxylation of 2,3-dihydrobenzoic acid to catechol is described by Pesci et al. in FEBS J. 2015, 282 (7), 1334-1345. Further possibly useful decarboxylases are described in WO2013/023999A1. The bacterial decarboxylation of o-phtalic acids has been described by Taylor et al. in Appl Environ Microbiol. 1983 December; 46(6):1276-81. Accordingly, enzymatic decarboxylation reactions can be suitably used.

A particular embodiment of the present invention is thus the preparation of bisphenol A, AP, AF, B, BP, C1, C2, E, F, TMZ or Z, preferably bisphenol A, B, C1, E, F or Z, comprising reacting a bisfuranic compound with the alkyne according to formula (IIIb), wherein $R_4$ and $R_5$ are independently selected from the group consisting of H, linear or branched $C_1$-$C_8$-alkyl, and EWG, wherein EWG is independently selected from the group consisting of —CN, —NO$_2$, —CO$_2$X, —C(O)NX, —C(=NY)X, CF$_3$, CCl$_3$, CBr$_3$, CI$_3$, —COH, —COX, —COF, —COCl, —COBr, —COI, wherein X and Y are independently selected from the group consisting of H, and linear or branched $C_1$-$C_8$-alkyl, optionally substituted with halogens and optionally polymer-supported; followed by a decarboxylation reaction or a reduction reaction.

In the embodiments wherein a product according to formula Vb is obtained and one or more of $R_2$, $R_4$ and $R_5$ is an EWG selected from the group consisting of —CN, —CO$_2$X, —C(O)NX, —C(=NY)X, —COH, —COX, —COF, —COCl, —COBr and —COI, it may be preferred to reduce the EWG to a methyl group. In particular, in the embodiment wherein a product according VIIc is obtained and $R_5$ is an EWG selected from the group consisting of —CN, —CO$_2$X, —C(O)NX, —C(=NY)X, —COH, —COX, —COF, —COCl, —COBr and —COI, a reduction of $R_5$ to a methyl group is preferred to obtain for instance bisphenol C if $R_1$ is —C(Me)$_2$-.

If an alkene is used and $R_2$ and $R_4$ are all hydrogen, the reaction between the dienophile and the bisfuranic compound preferably gives a bisphenyl compound, preferably with the formula:

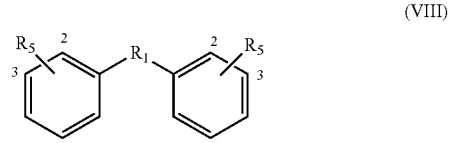

(VIII)

wherein in each phenyl group, $R_5$ is independently at the 2 or 3 position, giving as preferred products:

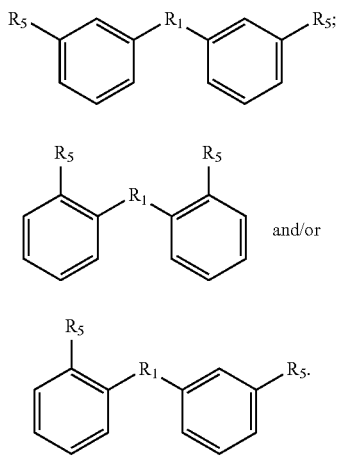

(VIIIa)

(VIIIb)

and/or (VIIIc)

For the compounds with formula V, VII and VIII, $R_1$ is preferably selected from a covalent bond or $R_{1A}$-$R_{1C}$:

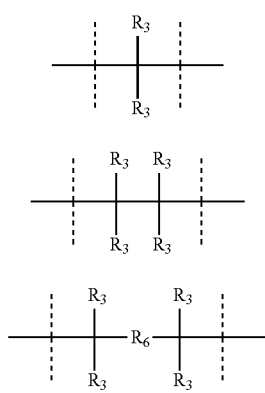

$R_{1A}$ $R_{1B}$ $R_{1C}$ wherein $R_3$ and $R_6$ are as for formula II.

For the compounds with formula Va or Vb wherein $R_5$ is not hydrogen, in particular with formula VIIIa and/or VIIIb, the method optionally comprises modification or removal of the $R_5$ group. For the compound with formula VIIIa or VIIIb, each $R_5$ is preferably —$CO_2X$, —CN, —COH, —$NO_2$, —$SO_2X$, or —$SO_3X$, with X as for EWG. Preferably, the modification of $R_5$ for the compound with formula Va, Vb, in particular VII, VIIIa or VIIIb involves hydrolysis, oxidation, reduction, nucleophilic addition, olefination, rearrangement, decarboxylation, decarbonylation and combinations thereof such that the final product has as $R_5$—H, linear or branched $C_1$-$C_8$-alkyl, —$CH=CH_2$, —$CO_2X$, —C(O)$NX_2$, —$CH_2OX$, —$CH_2NX_2$, —CHO, —OX, —CN, —$NO_2$, —C(O)NX, —C(=NY)X, —$CF_3$, —$CCl_3$, —$CBr_3$, —$CI_3$, —$SO_2X$, —$SO_3X$, —$NX_2$, —COX, —COF, —COCl, —COBr, or —COI, wherein X and Y are independently H, or linear or branched $C_1$-$C_8$-alkyl, optionally substituted with halogens and optionally polymer-supported.

Accordingly, if the bisfuranic compound has formula IIIc wherein $R_2$ is H, the product can for example have formula VIIIa or VIIIb with $R_{1C}$, preferably with the formula:

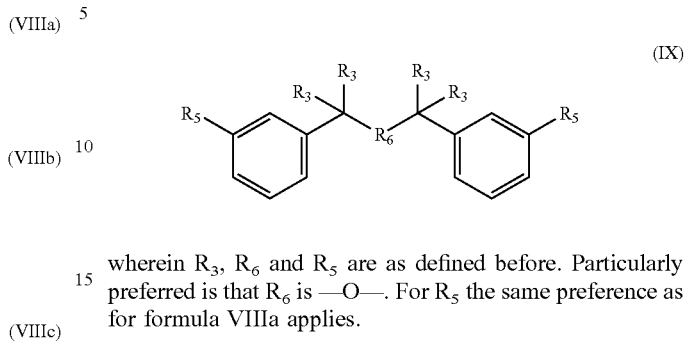

(IX)

wherein $R_3$, $R_6$ and $R_5$ are as defined before. Particularly preferred is that $R_6$ is —O—. For $R_5$ the same preference as for formula VIIIa applies.

In an attractive embodiment, the dienophile comprises acryl-sulfonic acid and/or derivatives thereof, such that the dienophile is an alkene with formula IIIa, wherein $R_4$ is hydrogen and $R_5$ is —$SO_3X$ wherein X is H or linear or branched $C_1$-$C_8$-alkyl, optionally substituted with halogens, optionally supported on a polymer or other heterogeneous support. In this way, the method yields a di-sulfonate compound comprising two phenyl groups. Such di-aromatic di-sulfonate compounds are potentially useful as plasticizers, crosslinking agents, surfactants and other such applications.

Accordingly, the method for example comprises reacting a bisfuranic compound with $R_1$ as mentioned with an alkene dienophile wherein $R_4$ is hydrogen and $R_5$ is or comprises —$SO_3X$, wherein the bisfuranic compound is preferably according to any of formula IIa-IId. Preferably, the method gives as product a compound with formula Va, in particular with formula VIII, especially with formula VIIIa, VIIIb and/or VIIIc, preferably according to formula IX, wherein each $R_5$ is —$SO_3X$. In an aspect, the invention is also directed to such compounds and salts thereof.

Accordingly, the reaction may for example involve:

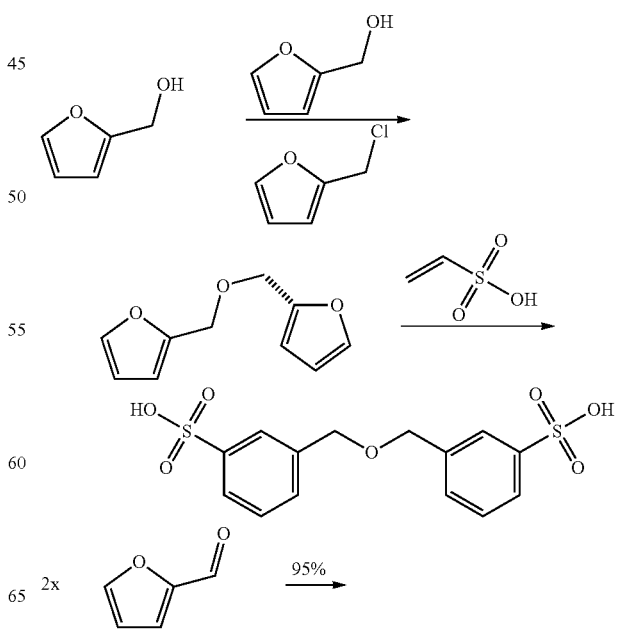

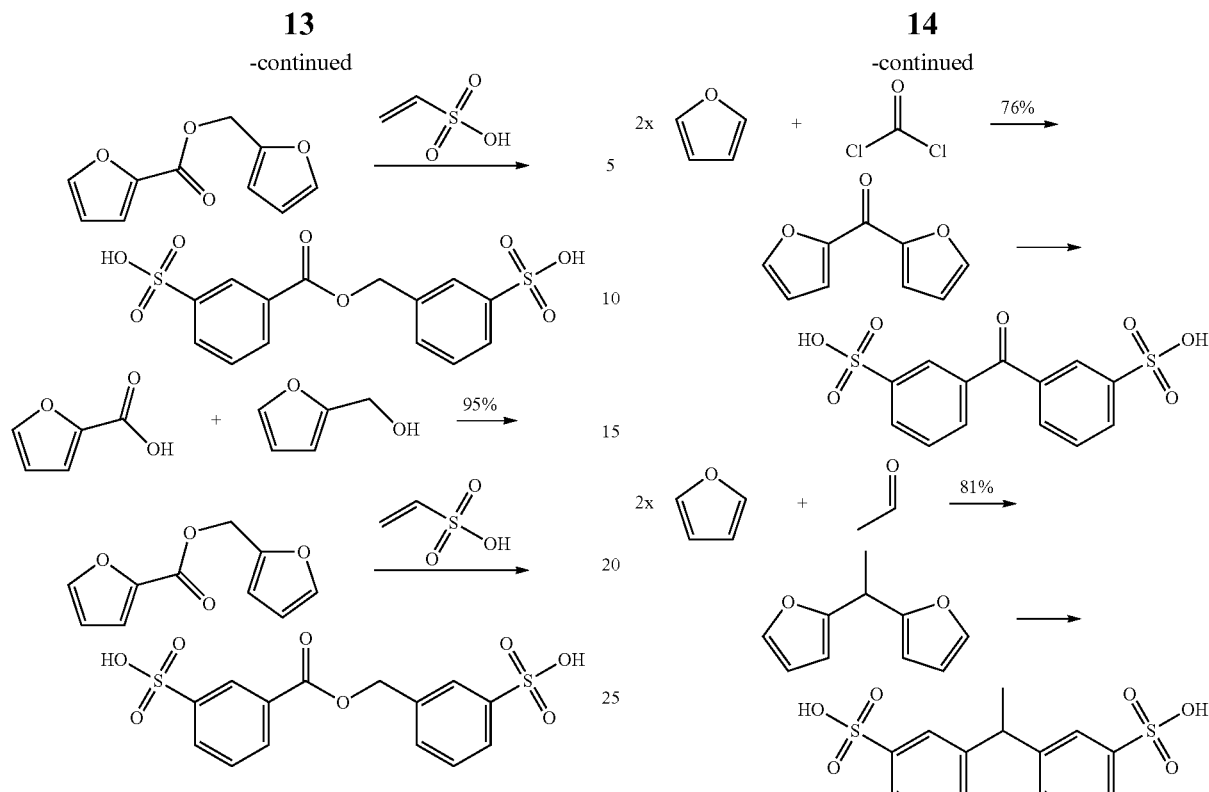
The reaction may also involve for example the following reactions wherein the dienophile is acryl-sulfonic acid:
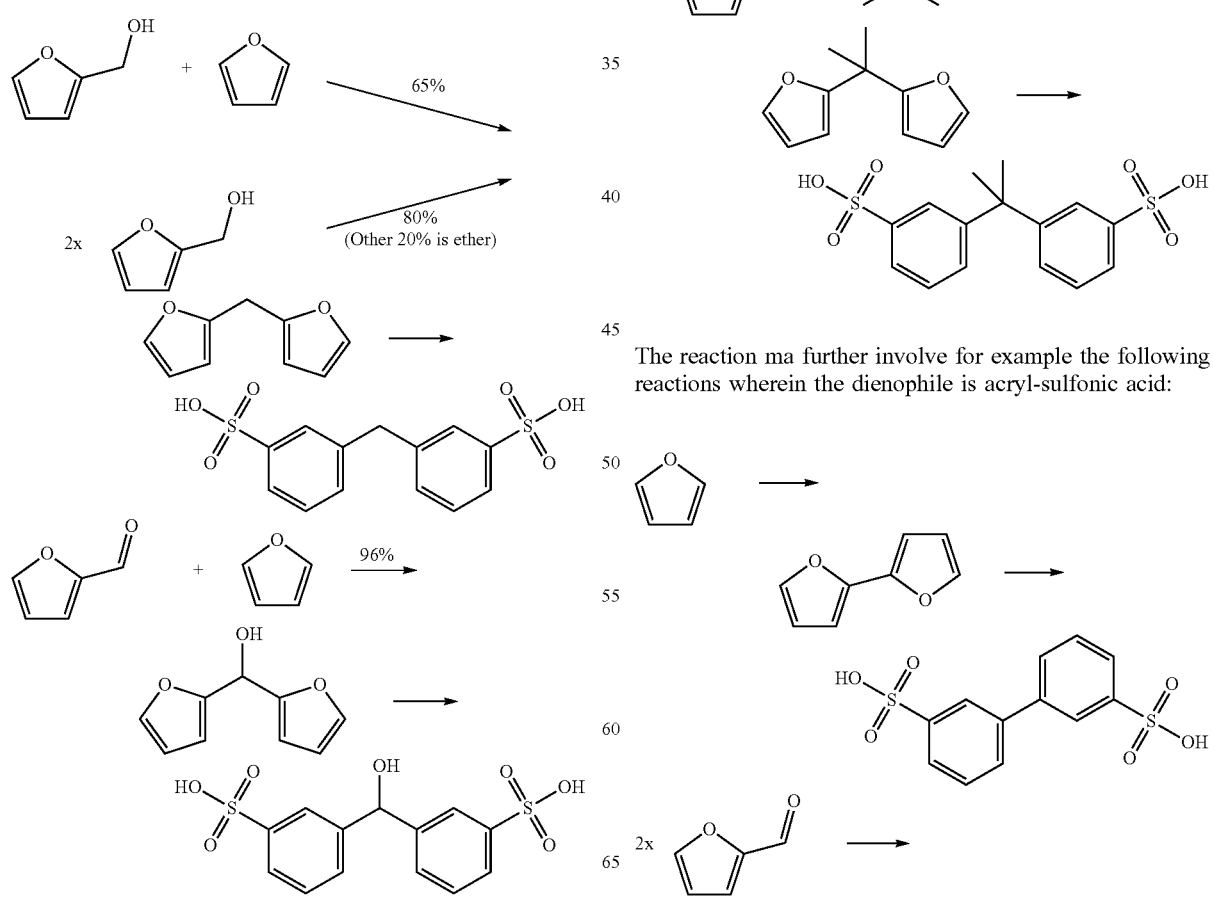
The reaction ma further involve for example the following reactions wherein the dienophile is acryl-sulfonic acid:

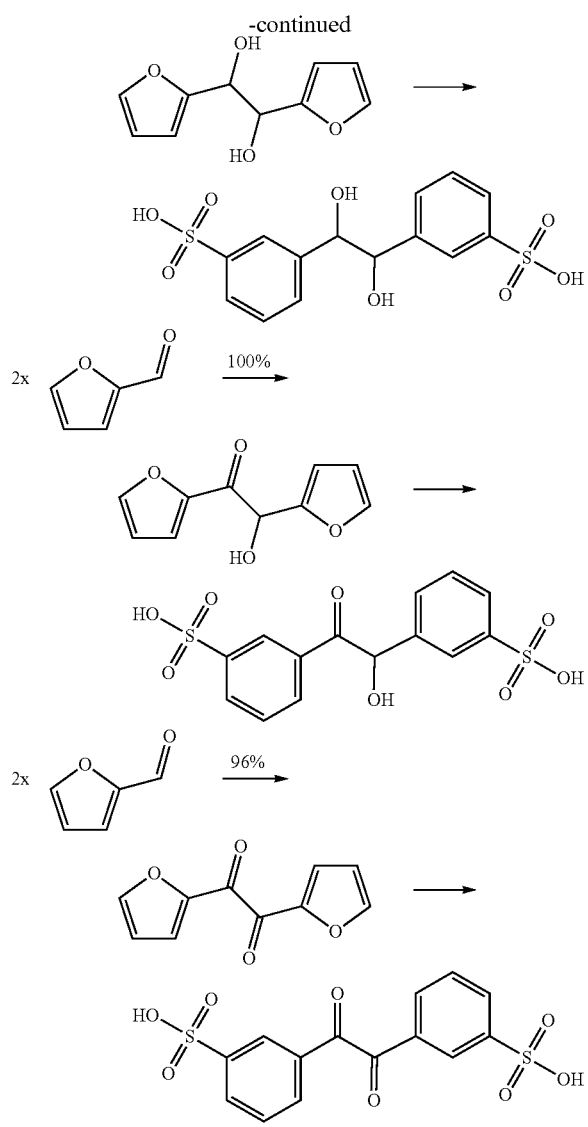

In these reactions, —SO$_3$H is indicated, however this can be also be —SO$_3$X wherein X is linear or branched C$_1$-C$_8$-alkyl, optionally substituted with halogens. The exemplified bisfuranic compounds can also be reacted with any dienophile.

Hence, in some embodiments, the method provides as product:

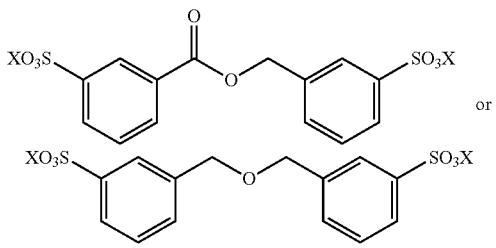

wherein X is H or linear or branched C$_1$-C$_8$-alkyl, optionally substituted with halogens.

In a particular embodiment of the present invention, the Diels-Alder reaction is catalyzed. Preferably the catalyst is a protic or a Lewis acid, optionally supported on a polymer or a heterogeneous support such as silica. More preferably the catalyst is a Lewis acid based on a metal, preferably a metal selected from the group consisting of Zn, Al, Sc, B, Fe, Ir, In, Hf, Sn, Ti, Yb, Sm, Cr, Co, Ni, Pb, Cu, Ag, Au, Tl, Hg, Pd, Cd, Pt, Rh, Ru, La, Ce, Pr, Nd, Pm, Eu, Gd, Tb, Dy, Ho, Er, Tm, Lu, V, Mn, Y, Zr, Nb, Mo, Ta, W, Re, Os and combinations thereof. Even more preferably, the catalyst is selected from the group consisting of ZnI$_2$, ZnBr$_2$, ZnCl$_2$, Zn(Ac)$_2$, Sc(OSO$_2$CF$_3$)$_3$, Y(OSO$_2$CF$_3$)$_3$, AlCl$_3$, A(Et)$_2$Cl, BCl$_3$, BF$_3$, B(Ac)$_3$, FeCl$_3$, FeBr$_3$, FeCl$_2$, Fe(Ac)$_2$, IrCl$_3$, HfCl$_4$, SnCl$_4$, TiCl$_4$ clays, zeolites and combinations thereof. Most preferably, the catalyst is selected from the group consisting of ZnI$_2$, ZnBr$_2$, ZnCl$_2$, Sc(OSO$_2$CF$_3$)$_3$, Y(OSO$_2$CF$_3$)$_3$, AlCl$_3$, A(Et)$_2$Cl, TiCl$_4$ and combinations thereof. The reaction can also be conducted without catalysis.

The Diels-Alder reaction can be performed for example at a temperature ranging from −60 to 350° C., preferably −20 to 250° C., more preferably 20 to 180° C. The precise temperature depends on the specific bisfuranic compound and dienophile used.

The dienophile is for example provided in about 1 equivalent per furanic group of the bisfuranic compound, giving a molar ratio of dienophile to bisfuranic compound of for example at least 2:1.

The Diels-Alder reaction may be performed by a pressure ranging from 0-200 bar, preferably 1-50 bar.

The Diels-Alder reaction is typically performed in a suitable solvent, preferably in a concentration of 0.1-3 M, more preferably about 2 M, selected from the group consisting of water, alcohols, esters, ketones, aliphatic hydrocarbons, aromatic hydrocarbons, organic acids, ethers, diprotic apolar solvents, halogenated solvents, nitrated solvents, ionic liquids, organic bases and combinations thereof.

In a particular embodiment of the present invention, furanics derivable from C4-sugars are used for preparing the bisfuranic compound. Typically, C4-sugars are converted into furan.

In another particular embodiment of the present invention, a furanic compound derivable from C5-sugars is used for preparing the bisfuranic compound. Typically, C5-sugars are converted into mono-substituted furan, for example with a substituent selected from the group consisting of Me, F, Cl, Br, I, —CH$_2$F, —CH$_2$Cl, —CH$_2$Br, —CH$_2$I, —CH$_2$NH$_2$ and amides thereof, —CH$_2$OH and esters or ethers thereof, —COH, and —CO$_2$H and esters thereof.

In yet another particular embodiment of the present invention, furanic compounds derivable from C6-sugars are used for preparing the bisfuranic compound. Usually C6-sugars are converted into bis-substituted furan, for example wherein the substituents are independently selected from the group consisting of Me, F, Cl, Br, I, —CH$_2$F, —CH$_2$Cl, —CH$_2$Br, —CH$_2$I, —CN, —NO$_2$, —CH$_2$NH$_2$ and amides thereof, —CH$_2$OH and esters or ethers thereof, —COH, and —CO$_2$H and esters thereof. The bisfuranic compound can also be obtained from compounds of petrochemical origin.

The method can optionally comprise obtaining a furanic compound from biomass or from material obtained from biomass and can also optionally comprise preparing a bisfuranic compound from at least said furanic compound.

Preferably the method comprises further reacting the bisphenyl compound in one or more reactions selected from the group consisting of hydrolysis, reduction, oxidation, decarboxylation, decarbonylation, nucleophilic addition, olefination, rearrangement and combinations thereof. In a particular embodiment of the present invention wherein the bisphenyl compound is a compound according to formula Va or Vb, this reaction generally involves conversion of $R_2$, $R_4$ and/or $R_5$ and/or the hydroxyl group, preferably with one or more of said reactions.

The method may further comprise removing substituents from the formed phenyl groups, preferably comprising removing all substituents other than hydroxyl For the purpose of clarity and a concise description features are described herein as part of the same or separate embodiments, however, it will be appreciated that the scope of the invention may include embodiments having combinations of all or some of the features described.

The invention may be illustrated by the following examples.

EXAMPLE 1

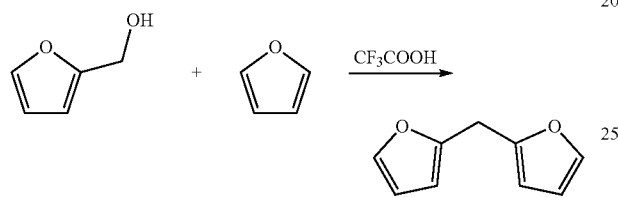

To a reactor was charged furfuryl alcohol (9.65 ml) and the stirring was started. Furan (145 ml) was then charged to the reactor. The mixture was cooled to 1° C., then trifluoroacetic acid (10 g) was dropwise. This was stirred for 36 hours at 1° C. then the mixture was washed with aqueous saturated sodium bicarbonate solution (2×200 ml), then the organics were dried ($MgSO_4$) filtered, and reduced to an viscous liquid by rotary evaporation. This crude mixture was then subjected to distillation, with the collected product distilling at a head temperature of 76° C. and a pressure of 16 mbar. This yielded 2,2'-difurylmethane as a light yellow liquid (9.89 g, 60%). The structure was confirmed by 1H NMR.

EXAMPLE 2

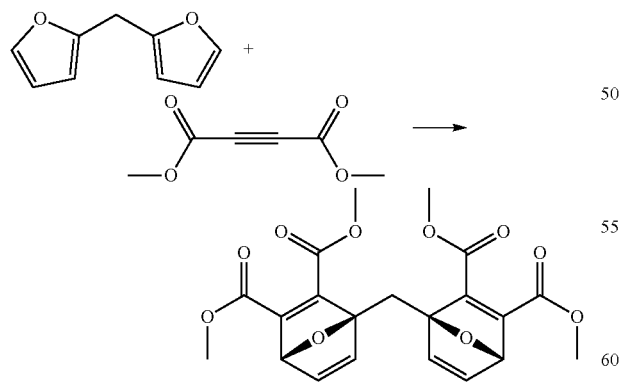

2,2'-difurylmethane (715 mg) was charged to a reactor, then dimethyl acetylenedicarboxylate (1.8 ml) was added. The reactor was sealed, and the mixture was heated to 110° C., with stirring, for 2 hours. The reaction mixture was cooled to room temperature, and the reaction mixture was purified by flash chromatography to give the desired product as a yellow gum (1.57 g, 76%). The structure was confirmed by 1H NMR.

EXAMPLE 3

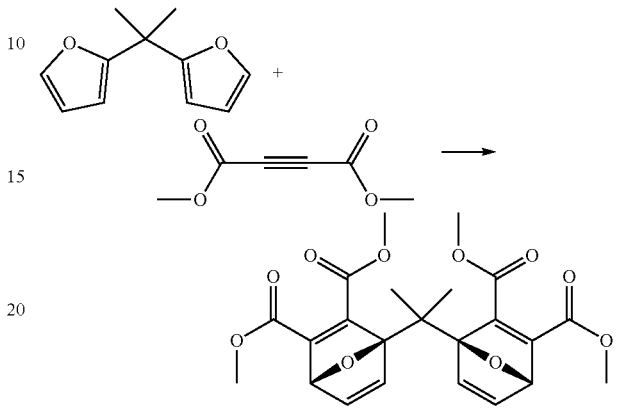

2,2'-difurylpropane (1 g) was charged to a reactor, then dimethyl acetylenedicarboxylate (2.1 ml) was added. The reactor was sealed, and the mixture was heated to 110° C., with stirring, for 2 hours, then 150° C. for 30 minutes. The reaction mixture was cooled to room temperature, and the reaction mixture was purified by flash chromatography to give the desired product as a light yellow gum (2.3 g, 88%). The structure was confirmed by 1H NMR.

EXAMPLE 4

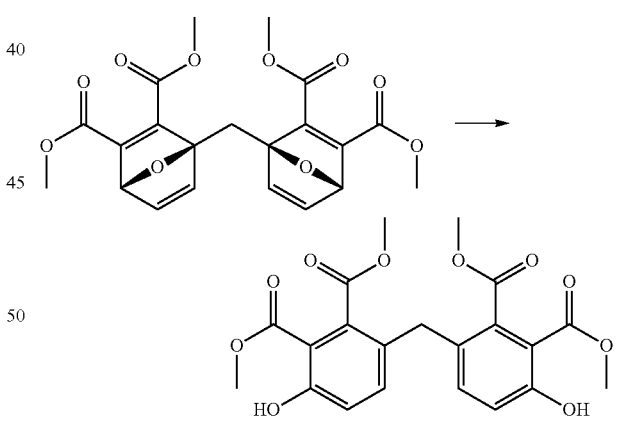

The product of the Diels-Alder reaction between 2,2'-difurylmethane (1039 mg) was charged to a reactor, then methanol (20 ml) was added and the mixture stirred until solution was achieved. To this was charged concentrated sulfuric acid (500 μL), and the reactor was sealed, heated to 130° C., and held for 6 hours. The reaction mixture was cooled to 20° C., then the reaction mixture was diluted with dichloromethane (20 ml). The solution was then washed with aqueous saturated sodium bicarbonate solution (2×20 ml), then the organics were dried ($MgSO_4$) filtered, and reduced to an viscous liquid by rotary evaporation. This liquid was purified by flash chromatography to give the desired product as a light yellow solid (631 mg, 60%). The structure was confirmed by 1H NMR.

EXAMPLE 5

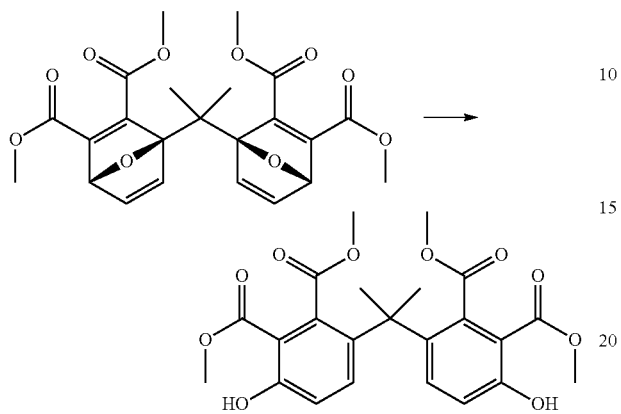

The product of the Diels-Alder reaction between 2,2'-difurylpropane (1.9 g) was charged to a reactor, then methanol (10 ml) was added and the mixture stirred until solution was achieved. To this was charged concentrated sulfuric acid (500 µL), and the reactor was sealed, heated to 130° C., and held for 6 hours. The reaction mixture was cooled to 20° C., then the reaction mixture was diluted with dichloromethane (20 ml). The solution was then washed with aqueous saturated sodium bicarbonate solution (2×20 ml), then the organics were dried (MgSO$_4$) filtered, and reduced to an viscous liquid by rotary evaporation. This liquid was was purified by flash chromatography to give the desired product as a brown gum (1443 mg, 75%). The structure was confirmed by 1H NMR.

EXAMPLE 6

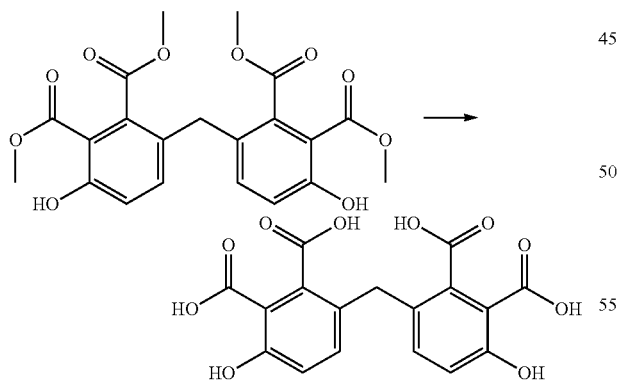

To a reactor was charged the tetra-ester product (500 mg) and methanol (3.6 ml) and this was dissolved with stirring. To this was added 4M aqueous sodium hydroxide solution (3.6 ml) and the reaction mixture was heated to 60° C. and held for 4 hours. The reaction mixture was cooled to 20° C. then washed with DCM (2×10 ml). The aqueous layer was then acidified to pH~1 with concentrated sulfuric acid, then the organics were extracted twice with EtOAc (2×15 ml). The combined organics were dried (Na$_2$SO$_4$), filtered and reduced to yield the desired product as a light brown gum (383 mg, 88%). The structure was confirmed by 1H NMR.

EXAMPLE 7

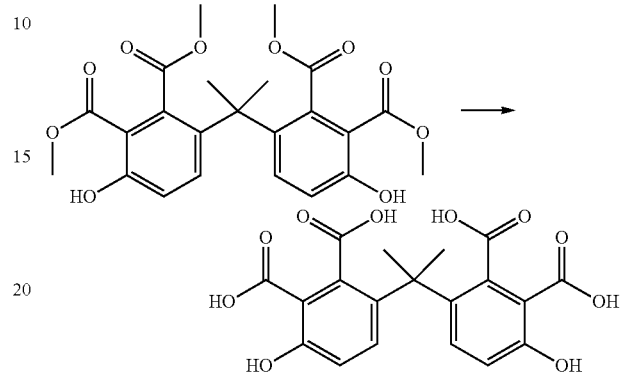

To a reactor was charged the tetra-ester product (750 mg) and methanol (5.1 ml) and this was dissolved with stirring. To this was added 4M aqueous sodium hydroxide solution (5.1 ml) and the reaction mixture was heated to 60° C. and held for 4 hours. The reaction mixture was cooled to 20° C. then washed with DCM (2×10 ml). The aqueous layer was then acidified to pH~2 with concentrated sulfuric acid, then the organics were extracted twice with EtOAc (2×15 ml). The combined organics were dried (Na$_2$SO$_4$), filtered and reduced to yield the desired product as a brown gum (540 mg, 82%). The structure was confirmed by 1H NMR.

EXAMPLE 8

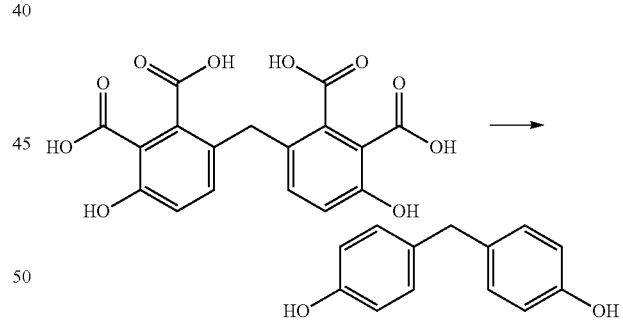

A reactor was charged with the 4,4'-methylenebis[phenol-2,3-dicarboxylic acid] starting material (300 mg), copper(I) oxide (24 mg), 1,10-phenanthroline (60 mg), NMP (1200 µL) and quinoline (330 µL). The reactor was sealed, heated to 190° C. with microwave heating, and held for 1 hours, with stirring. The reaction mixture was cooled to ambient temperature then added to a stirred 1M solution of aqueous hydrochloric acid, and the organics were extracted with ethyl acetate (2×10 ml). The combined organics were washed with water, dried (Na$_2$SO$_4$), filtered and reduced by rotary evaporation to obtain the desired product as a light brown oil (101 mg, 63%). The structure of the product as bisphenol F (bis(4-hydroxyphenyl)methane) was confirmed by 1H NMR.

EXAMPLE 9—DECARBOXYLATION WITH MODEL COMPOUNDS

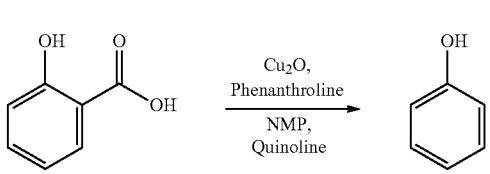 [SMILES: O=C(O)c1ccccc1O ; Oc1ccccc1]

A reactor was charged with 2-hydroxybenzoic acid (91 mg), copper(I) oxide (10 mg), 1,10-phenanthroline (24 mg), NMP (1 ml) and quinoline (364 mg, 333 µL). The reactor was sealed, heated to 165° C., and held for 40 hours, with stirring. The reaction mixture was cooled to ambient temperature then brought directly onto silica and purified by flash chromatography, eluting with n-hexane and ethyl acetate. Appropriate fractions were collected for the product peak and were reduced by rotary evaporation to yield a yellow liquid. This was dissolved in dichloromethane (10 ml) and washed with 1N aqueous hydrochloric acid solution (2×10 ml) and subsequently with water (10 ml). The combined aqueous phase was extracted with dichloromethane (3×5 ml). All the organic phases were combined and dried (MgSO$_4$), filtered, and reduced by rotary evaporation to obtain the desired product as orange oil (21 mg, 33%). The structure was confirmed as phenol by 1H NMR.

EXAMPLE 10—DECARBOXYLATION WITH MODEL COMPOUNDS

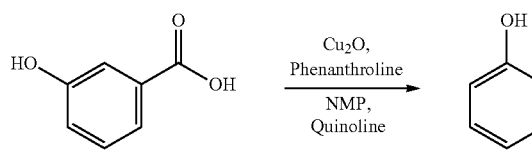

A reactor was charged with 3-hydroxybenzoic acid (91 mg), copper(I) oxide (10 mg), 1,10-phenanthroline (24 mg), NMP (1 ml) and quinoline (364 mg, 333 µL). The reactor was sealed, heated to 165° C., and held for 40 hours, with stirring. The reaction mixture was cooled to ambient temperature then brought directly onto silica and purified by flash chromatography, eluting with n-hexane and ethyl acetate. Appropriate fractions were collected for the product peak and were reduced by rotary evaporation to yield a yellow liquid. This was dissolved in dichloromethane (10 ml) and washed with 1N aqueous hydrochloric acid solution (2×10 ml) and subsequently with water (10 ml). The combined aqueous phase was extracted with dichloromethane (3×5 ml). All the organic phases were combined and dried (MgSO$_4$), filtered, and reduced by rotary evaporation to obtain the desired product as orange oil (65 mg, 50%). The structure was confirmed as phenol by 1H NMR.

EXAMPLE 11—DECARBOXYLATION WITH MODEL COMPOUNDS

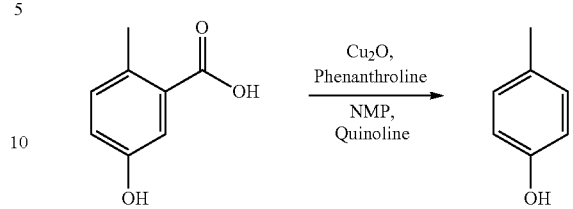

A reactor was charged with 5-hydroxy-2-methylbenzoic acid (100 mg), copper(I) oxide (10 mg), 1,10-phenanthroline (24 mg), NMP (1 ml) and quinoline (364 mg, 333 µL). The reactor was sealed, heated to 170° C., and held for 40 hours, with stirring. The reaction mixture was cooled to ambient temperature then brought directly onto silica and purified on a Reveleris® X2 Flash Chromatography System, eluting with n-hexane and ethyl acetate. Appropriate fractions were collected for the product peak and were reduced by rotary evaporation to yield a yellow liquid. This was dissolved in dichloromethane (10 ml) and washed with 1N aqueous hydrochloric acid solution (2×10 ml) and subsequently with water (10 ml). The combined aqueous phase was extracted with dichloromethane (3×5 ml). All the organic phases were combined and dried (Na$_2$SO$_4$), filtered, and reduced by rotary evaporation to obtain the desired product as orange oil (33 mg, 47%). The structure was confirmed as 4-methylphenol by 1H NMR.

The invention claimed is:

1. A method for preparing a compound comprising two phenyl groups by reacting a bisfuranic compound with a dienophile, wherein the dienophile is an alkyne or an alkene and wherein the bisfuranic compound is according to any of the formulae (IIa-IId)

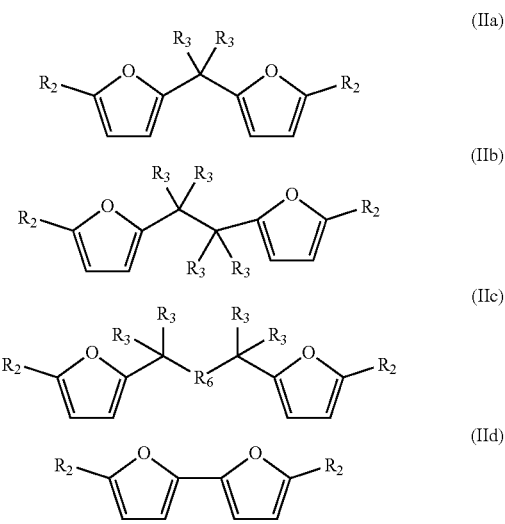

wherein the furanic moieties are optionally substituted, and wherein each $R_2$ is independently H, a heteroatom, a halogen, or linear or branched $C_1$-$C_8$ alkyl, wherein said alkyl is optionally further substituted by halogens and/or heteroatoms, each $R_3$ is independently selected from the group consisting of H, a halogen, a heteroatom functional group, and optionally with halogen or heteroatom substituted and/or optionally heteroatom containing $C_1$-$C_{40}$ hydrocarbyl group, wherein two of said $R_3$ groups can be joined to form a ring, or wherein two of said $R_3$ groups on the same atom are combined to form a substituent having a double bond with said atom, and wherein $R_6$ is selected from the group consisting of a heteroatom functional group and optionally with halogen or heteroatom substituted and/or optionally heteroatom containing $C_1$-$C_{40}$ hydrocarbyl group.

2. The method according to claim 1, wherein the dienophile is an alkene according to formula (IIIa) or an alkyne according to formula (IIIb) or

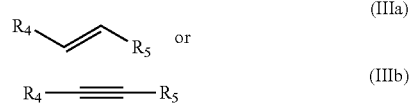

wherein $R_5$ is an electron withdrawing group EWG, and in case of an alkyne according to formula (IIIb), $R_5$ is EWG or selected from the same group as $R_3$,
wherein $R_4$ is H, linear or branched $C_1$-$C_8$ alkyl, or EWG,
wherein EWG is independently selected from the group consisting of —CN, —$NO_2$, —$CO_2X$, —C(O)NX, —C(=NY)X, $CF_3$, $CCl_3$, $CBr_3$, $Cl_3$, —$SO_2X$, —$SO_3X$, —COH, —COX, —COF, —COCl, —COBr, —COI, wherein X and Y are independently selected from the group consisting of H and linear or branched $C_1$-$C_8$ alkyl, optionally substituted with halogens and optionally polymer-supported.

3. The method according to claim 2, wherein R4 is hydrogen.

4. The method according to claim 2, wherein the bisfuranic compound comprises a backbone structure according to formula (I)

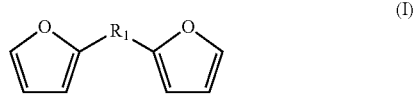

wherein $R_1$ is a linking group or is a covalent bond, and wherein the furanic moieties are optionally substituted,
wherein the dienophile is an alkyne according to formula (IIIb) and wherein the compound comprising two phenyl groups is a bisphenol compound according to formula (VII):

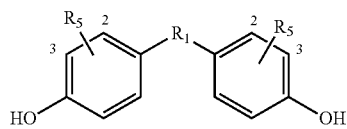

wherein in each phenyl group, $R_5$ is independently at the 2 or 3 position.

5. The method according to claim 2, wherein an alkyne dienophile is used and wherein the product is a bisphenol.

6. The method according to according to claim 2, wherein the dienophile is an alkene with formula (IIIa), wherein $R_4$ is H and $R_5$ is —$SO_3X$, wherein X is H or linear or branched $C_1$-$C_8$ alkyl, optionally substituted with halogens.

7. The method according to claim 1, wherein the reaction is catalysed with a Lewis acid.

8. The method according to claim 1, comprising further reacting the compound comprising two phenyl groups in one or more reactions selected from the group consisting of hydrolysis, reduction, oxidation, decarboxylation, decarbonylation, nucleophilic addition, olefination, rearrangement and combinations thereof.

9. The method according to claim 1, further comprising removing substituents from the formed phenyl groups.

10. A compound having formula (IX):

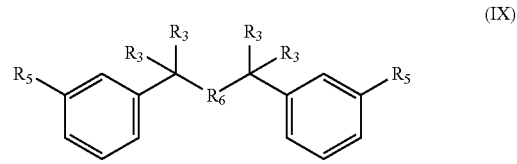

wherein each $R_5$ is —COH, —$SO_2X$, or —$SO_3X$, wherein X is H or linear or branched $C_1$-$C_8$ alkyl, said linear or branched $C_1$-$C_6$ alkyl substituted with halogens,
wherein $R_6$ is O, and
and wherein $R_3$ is as defined in claim 1, or a salt thereof.

11. A compound according to claim 10, having the formula

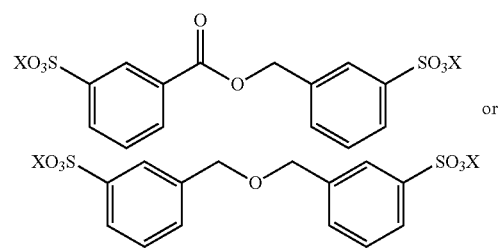

wherein X is H or linear or branched $C_1$-$C_8$ alkyl, optionally substituted with halogens, or a salt thereof.

12. The method according to claim 5, wherein the product is bisphenol A, AP, AF, B, BP, C1, C2, E, F, TMC or Z.

13. The method according to claim 9, comprising removing all substituents other than hydroxyl.

14. The method according to claim 12, wherein the product is bisphenol A, B, C1, E, F or Z.

* * * * *